(12) United States Patent
Kabir et al.

(10) Patent No.: US 10,183,270 B1
(45) Date of Patent: Jan. 22, 2019

(54) ENCAPSULATED PARTICULATE MATTERS IN A SOL-GEL SILICA MATRIX AND METHOD OF PREPARATION

(71) Applicants: Abuzar Kabir, Dhaka (BD); Kenneth G. Furton, Homestead, FL (US)

(72) Inventors: Abuzar Kabir, Dhaka (BD); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/818,836

(22) Filed: Nov. 21, 2017

(51) Int. Cl.
| | |
|---|---|
| *B01J 20/08* | (2006.01) |
| *B01J 20/12* | (2006.01) |
| *B01J 20/02* | (2006.01) |
| *B01J 20/26* | (2006.01) |
| *G01N 1/40* | (2006.01) |
| *B01D 53/04* | (2006.01) |
| *B01D 53/02* | (2006.01) |
| *B01D 15/10* | (2006.01) |

(Continued)

(52) U.S. Cl.
CPC ............... *B01J 20/08* (2013.01); *B01D 15/10* (2013.01); *B01D 53/025* (2013.01); *B01D 53/0407* (2013.01); *B01J 20/0211* (2013.01); *B01J 20/0251* (2013.01); *B01J 20/103* (2013.01); *B01J 20/12* (2013.01); *B01J 20/18* (2013.01); *B01J 20/20* (2013.01); *B01J 20/205* (2013.01); *B01J 20/24* (2013.01); *B01J 20/261* (2013.01); *B01J 20/262* (2013.01); *B01J 20/264* (2013.01); *G01N 1/405* (2013.01); *B01D 2253/104* (2013.01); *B01D 2253/106* (2013.01); *B01D 2253/1124* (2013.01); *B01D 2253/202* (2013.01); *B01D 2253/25* (2013.01)

(58) Field of Classification Search
CPC ........ B01J 20/08; B01J 20/205; B01J 20/261; B01J 20/103; B01J 20/18; B01J 20/24; B01J 20/262; B01J 20/12; B01J 20/0211; B01J 20/264; B01J 20/0251; B01J 20/20; B01D 53/0407; B01D 53/025; B01D 15/10; B01D 2253/25; B01D 2253/106; B01D 2253/1124; B01D 2253/202; B01D 2253/104; G01N 1/405
See application file for complete search history.

(56) References Cited

U.S. PATENT DOCUMENTS

| | | | |
|---|---|---|---|
| 8,754,182 B2 * | 6/2014 | Edmiston .................. | B09C 1/08 524/588 |
| 9,144,784 B2 * | 9/2015 | Edmiston ............... | B01J 20/265 |

* cited by examiner

*Primary Examiner* — Anthony J Zimmer
(74) *Attorney, Agent, or Firm* — Saliwanchik, Lloyd & Eisenschenk

(57) ABSTRACT

A particulate sorbent includes a carbonaceous and/of non-carbonaceous particulate matter encapsulated in sol-gel sorbent matrix where microparticles of a porous sol-gel metal oxide network display a high surface area with small cross-section pores and a nanoparticle or microparticle filler that is a carbonaceous and/or non-carbonaceous particulate matter. The particulate sorbent is prepared by dispersing carbonaceous and/of non-carbonaceous particulate matter in a mixture of a metal oxide precursor, water, catalyst and optionally a solvent and a polymer functionalized to react with the metal oxide precursor. Catalysis is by acid followed by base to separate hydrolysis in the sol with condensation to a gel to give a highly porous gel. The gel is subsequently fractured into sorbent particles. The sorbent particles can be used for sampling or separating analytes.

19 Claims, 18 Drawing Sheets

(51) Int. Cl.
*B01J 20/10* (2006.01)
*B01J 20/18* (2006.01)
*B01J 20/20* (2006.01)
*B01J 20/24* (2006.01)

| Elt. | Line | Intensity (c/s) | Conc | Units | Error 2-sig | MDL 3-sig | |
|---|---|---|---|---|---|---|---|
| C | Ka | 24.14 | 17.936 | wt.% | 1.848 | 1.326 | |
| O | Ka | 178.36 | 44.505 | wt.% | 1.508 | 0.354 | |
| Al | Ka | 14.43 | 0.786 | wt.% | 0.138 | 0.156 | |
| Si | Ka | 724.46 | 36.773 | wt.% | 0.617 | 0.137 | |
| | | | 100.000 | wt.% | | | Total |

| Elt. | Line | Intensity (c/s) | Conc | Units | Error 2-sig | MDL 3-sig | |
|---|---|---|---|---|---|---|---|
| O | Ka | 33.37 | 38.449 | wt.% | 2.976 | 4.464 | |
| Al | Ka | 0.87 | 0.318 | wt.% | 0.384 | 0.539 | |
| Si | Ka | 162.97 | 61.233 | wt.% | 2.169 | 0.495 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 111.50 | 51.303 | wt.% | 2.220 | 0.697 | |
| O | Ka | 53.49 | 25.137 | wt.% | 1.565 | 0.455 | |
| Si | Ka | 252.89 | 23.561 | wt.% | 0.673 | 0.178 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 502.04 | 98.137 | wt.% | 1.984 | 0.481 | |
| O | Ka | 1.12 | 1.540 | wt.% | 1.360 | 1.829 | |
| Si | Ka | 2.06 | 0.323 | wt.% | 0.218 | 0.297 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 12.03 | 19.858 | wt.% | 2.794 | 1.712 | |
| O | Ka | 46.46 | 28.533 | wt.% | 1.892 | 0.420 | |
| Si | Ka | 331.87 | 51.609 | wt.% | 1.281 | 0.287 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 239.75 | 87.151 | wt.% | 2.553 | 0.653 | |
| O | Ka | 6.24 | 12.296 | wt.% | 2.305 | 1.045 | |
| Al | Ka | 0.55 | 0.149 | wt.% | 0.268 | 0.386 | |
| Si | Ka | 1.51 | 0.404 | wt.% | 0.291 | 0.384 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 20.26 | 17.794 | wt.% | 2.039 | 1.556 | |
| O | Ka | 116.47 | 41.104 | wt.% | 1.736 | 0.518 | |
| Si | Ka | 390.66 | 41.102 | wt.% | 0.941 | 0.218 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 327.32 | 92.383 | wt.% | 2.311 | 0.550 | |
| O | Ka | 3.98 | 5.895 | wt.% | 1.621 | 1.435 | |
| S | Ka | 8.55 | 1.722 | wt.% | 0.348 | 0.349 | |
| | | | 100.000 | wt.% | | | Total |

| Elt. | Line | Intensity (c/s) | Conc | Units | Error 2-sig | MDL 3-sig | |
|---|---|---|---|---|---|---|---|
| C | Ka | 35.31 | 29.551 | wt.% | 2.364 | 1.228 | |
| O | Ka | 77.28 | 35.131 | wt.% | 1.819 | 0.520 | |
| Si | Ka | 303.21 | 35.317 | wt.% | 0.919 | 0.230 | |
| | | | 100.000 | wt.% | | | Total |

ENCAPSULATED PARTICULATE MATTERS IN A SOL-GEL SILICA MATRIX AND METHOD OF PREPARATION

BACKGROUND OF INVENTION

Traditionally, a large number of particulate matters are used individually or in different combinations as adsorbents in water filtration system, air pollutant trapping systems, sewerage treatment plants, to name a few. This particulate matters include activated carbon, metal-organic framework, carbon nanotube, biochar, iron oxide, alumina, titania, zirconia, tin oxide, graphene, beta-cyclodextrin, calixarenes, manganese oxide, poly(styrene-divinyl benzene), carboxen, fullerene, cation exchange resins, anion exchange resins, and zwitterionic resins. These particulate matters offer a large variety of intermolecular interactions towards analytes via µ-µ stacking interactions, cation-µ bonding interactions, electron donor-acceptor interactions, hydrophobic interactions, hydrogen bonding interaction, cation exchange, anion exchange, and dipole-dipole interactions depending on their functional characteristics. Advantageously, many of these particulate matters possess extremely high surface area but disadvantageously demonstrate a strong tendency to form agglomeration. In their pristine form, aggregation excludes a large portion of these particles' available surface area to analytes that by intermolecular and/or ionic interactions undergo adsorption onto the surface of the particulate matters. As a result, the adsorption capacities of many of these particulate materials remain largely unexploited in practical applications.

Surface-bonded inorganic/hybrid organic-inorganic polymer coatings and monolithic beds are popular sorbents. These systems display high chemical stability and offer a diverse array of extracting phases for solvent-free/solvent minimized analytical sample preparation. The availability of a wide variety of sol-gel precursors and sol-gel active organic polymers allow facile synthesis of advanced material systems with unique selectivity, enhanced extraction sensitivity and high thermal, mechanical and solvent stability. This sol-gel derived inorganic/hybrid organic-inorganic advanced material system have been shown to be effective in solvent free/solvent minimized sample preparation for a wide variety of analytes with biological, environmental, clinical, toxicological, food, pharmaceutical, bio-analytical, and forensic significance.

Sol-gel technology is adaptable to forming multi-component materials that have customized surface morphologies, selectivities and affinities of the sorbent. A wide variety of sol-gel silica, titania, zirconia, alumina, and germania-based precursors are commercially available. Additionally, a wide range of sol-gel reactive organic ligands are available to design inorganic/hybrid organic-inorganic sol-gel coatings or monolithic beds that can be used to target a particular analyte or sample matrix with improved selectivity, sensitivity, extraction phase stability and performance.

To this end a carbonaceous or non-carbonaceous particulate matter encapsulated in sol-gel sorbent matrix has the potential to provide selective and efficient sorbents. The encapsulation of particulate matters in sol-gel inorganic matrix successfully prevents their agglomeration; on the other hand, the encapsulation of particulate matters in sol-gel hybrid organic-inorganic matrix synergistically extends the affinity and selectivity of the composite sorbent towards the target analyte(s). Such effect can't be achieved by using only the pristine particulate matters, sol-gel inorganic matrix (e.g., sol-gel silica) or sol-gel hybrid organic-inorganic (sol-gel silica bonded to organic polymer) matrix.

BRIEF SUMMARY

Embodiments of the invention are directed to particulate sorbents that has a carbonaceous and/or non-carbonaceous nanoparticle or microparticle encapsulated in a sol-gel sorbent matrix including microparticles of a porous sol-gel metal oxide network that has a high surface area with small cross-section pores. The metal oxide can be a silicate, an aluminate, a titanate, a zirconate, a germinate, or any combination thereof. A portion of the metals of the metal oxide are substituted with one or more $C_1$ to $C_4$ alkyl group and/or one or more aryl groups. The sol-gel metal oxide network comprises a plurality of polymer segments. One or more of the $C_1$ to $C_4$ alkyl group and/or one or more of the aryl groups can be substituted with a functional group. The sol-gel metal oxide network can comprise a plurality of polymer segments. The polymer segments can bridge between two or more metal oxide units.

Another embodiment of the invention is directed to a method of preparing the particulate sorbent, where a plurality of carbonaceous and/or non-carbonaceous nanoparticles of microparticles, a plurality of metal oxide precursors, and optionally, a plurality of polymer comprising at least one functional group capable of undergoing reaction with the metal oxide precursor are combining, optionally, with a solvent to make a sol mixture. Water and an acid catalyst mixed with to the sol mixture to hydrolyze the plurality of metal oxide precursors to form a hydrolyzed sol mixture. A base is added to the hydrolyzed sol mixture to condense the hydrolyzed sol mixture to a gel. The gel is then fractured into sorbent particles of a carbonaceous and/of non-carbonaceous nanoparticles of microparticles encapsulated in a sol-gel sorbent matrix. The metal oxide precursors have the structure: $M(R_1)(R_2)(R_3)(R_4)$ where, M is silicon, titanium, aluminum, zirconium, germanium, barium, gallium, indium, thallium, vanadium, cobalt, nickel, chromium, copper, iron, zinc, or boron, $R_1$, $R_2$, $R_3$ and $R_4$ are substituents groups, at least two of which are alkoxy, hydroxy, halide, or dialkylamino, and the remaining $R_1$, $R_2$, $R_3$ and $R_4$ are independently absent or comprise alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof. The polymer can be polydimethylsiloxane, polytetrahydrofuran, homopolymers or copolymers comprising polydimethylsiloxane (PDMS), polytetrahydrofuran (polyTHF), polyethyleneoxide, poly(caprolactone-block-dimethylsiloxane-black-caprolactone) triblock copolymer, 2-hydroxymethyl-8-crown-6, Beta-cyclodextrin, Calix[8]arene, poly(caprolactone-block-tetrahydrofuran-block caprolactone) triblock copolymer, poly(propylene glycol)-block-poly(ethylene glycol)-block-(polypropylene glycol), poly(caprolactone diol), poly(caprolactone triol), chitosan, Dimethylsiloxane-ethylene oxide block copolymer, Carbowax 20M, UCon HTF 14, Chitin, Poly(ethylene glycol)-poly(propylene glycol)-poly(ethylene glycol), and poly(propylene glycol)-poly(ethylene oxide)-poly(propylene glycol), sucrose, or sorbitol. Fracturing can be carried out by grinding or milling.

Other embodiments of the invention are directed to a method of collecting or separating, where a particulate sorbent is contacted with a fluid comprising analytes. The particulate sorbent can be added to the fluid. The method can be a solid phase extraction or a solid phase microextraction.

DETAILED DISCLOSURE

Figure 1:
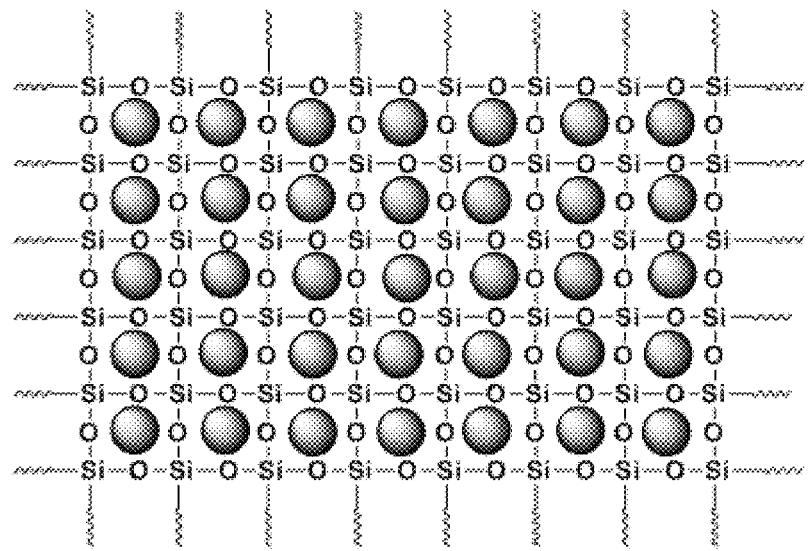
FIG. 1 shows a schematic representation of a carbonaceous or non-carbonaceous particulate matter encapsulated in sol-gel sorbent matrix, according to an embodiment of the invention.

Embodiments of the invention are directed to a method to form carbonaceous and non-carbonaceous particulate matters encapsulated in sol-gel sorbent matrices. The agglomeration of particulate matters can be inhibited by encapsulated them into sol-gel silica network. Sol-gel chemistry provides a convenient and mild reaction pathway to create pure silica or organically modified silica 3-D networks. Addition of sol-gel active organic polymer(s) as an additive in the sol solution during the sol-gel synthesis is also a common practice to engineer the selectivity of the resulting sol-gel sorbents. Addition of particulate matters in the sol solution during sol-gel synthesis results in a sol-gel composite sorbent system with homogeneously trapped particulate matters in a permeable cage-like architecture. Due to the inherently porous and open architecture of a sol-gel silica network, encapsulated particulate matters maintain high surface area and freely accessible interaction sites. This synergistic combination of silica chemistry, organic polymer chemistry as well as the chemistry of particulate matters result in robust composite material systems capable of exerting intermolecular/ionic interactions towards a wide variety of analytes including polar, medium polar, nonpolar, ionic, and metal species and successfully trap them in the sol-gel composite sorbent matrices when applied them in water filtration, environmental pollution remediation, waste water treatment, air pollution monitoring and mitigation, to name a few.

The encapsulated particulate matter retains the material properties of well-established particulate materials, such as: metals oxides including alumina, titania, and zirconia; carbonaceous materials including biochars, graphene, carbon nanotubes, activated carbons, Carboxen, and Caropack; and organic polymeric materials including polystyrene-divinylbenzene ion exchange resins, into sol-gel inorganic/hybrid inorganic-organic solid phase extraction sorbents. The unique combination of the particulates into sol-gel matrix synergistically augments the material properties of the composite material system to offer unique selectivity and affinity towards most of the target analytes. These analytes include emerging pollutants, EPA priority pollutants, heavy metals, ionic and ionizable compounds, endocrine disrupting chemicals, and other pollutants and unwanted entities in water and air. The efficient and robust sol-gel encapsulated particulate matter can be employed in point of use water filtration, for air pollution monitoring and mitigation, for water pollution monitoring and mitigation, for adsorbents in sewerage treatment, as sorbents in solid phase extraction, and as sorbents in solid phase microextraction. The particulate matters encapsulated in sol-gel silica matrix possess high porosity, high surface area, superior chromatographic selectivity, excellent extraction efficiency, and high thermal and chemical stability. The pore volume is 0-1.0 m$^3$/g. The surface area can be 1-2000 m$^2$/g. The pores can be micropores or mesopores or a combination thereof.

The sol-gel matrix can be any sol-gel formed by acid and/or base catalysis conversion of a sol comprising at least one metal oxide precursor. The metal oxide precursors for inclusion in the sol can be selected from precursors for silicates, aluminates, titanates, zirconates, germinates, other metal oxide precursors, or any mixture thereof. The nature of the metal oxide precursors is herein exemplified by silanes, but the equivalent with other metals and number of substituents can be readily appreciated by practitioners of the art. For, example, silicate based sol-gel the precursors can be a combination of tetraalkoxysilanes, trialkoxysilanes, and dialkoxysilanes. The proportion of tetraalkoxysilanes can be 0-100 weight percent. The proportion of triakoxysilanes can be 0 to 100 weight percent. The proportion of dialkoxysilanes can be 0 to 96 weight percent.

the metal oxide precursor has the structure:

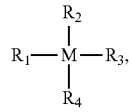

wherein, M is silicon, titanium, aluminum, zirconium, germanium, barium, gallium, indium, thallium, vanadium, cobalt, nickel, chromium, copper, iron, zinc, or boron, $R_1$, $R_2$, $R_3$ and $R_4$ are substituents groups, at least two of which are alkoxy, hydroxy, halide, or dialkylamino, and the remaining $R_1$, $R_2$, $R_3$ and $R_4$ independently absent or comprise alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof.

The silica precursor can be any reactive silane compatible with any solvent of the sol and other components of the sol. The silane can be a tetraalkoxysilane, tetraacetoxysilane, tetrachlorosilane, tetradialkylaminosilane or any other silica precursor. For example, tetramethoxysilane or tetraethoxysilane can be used as a silica precursor. In like manner, a tetraalkoxytitanate can be used as a titania precursor, trialkoxyaluminum can be used as an alumina precursor, and other metal alkoxides can be the source of zirconia, germania, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or barium oxide.

Tetraalkoxysilanes, can be, but are not limited to, tetramethoxysilane and tetraethoxysilane. Tetraalkoxysilanes can be used exclusively with the polar organic molecules or with mixtures of trialkoxysilanes or dialkoxysilanes. The trialkoxysilanes can be, but are not limited to, alkyltrialkoxysilanes, such as methyltrimethoxysilanes, ethyltrimethoxysilanes, methyltriethoxysilanes, ethyltrialkoxysilanes, or any $C_xH_{2x+1}Si(OC_yH_{2y+1})_3$ silane, where x is 1 to 20 and y is 1 to 3. The alkyltrialkoxy silane can have a substituted alkyl group, for example, but not limited to, 3-aminoporpyltrimethoxysilane, 2-aminopropyltrimethoxysilane, 3-hydroxytrimethoxysilane, or any alkyl group containing one or more ether, hydroxyl, carboxylic acid, carboxylic amide, amino, alkylamino, dialkylamino, cyano group, or any other polar or non-polar groups. The trialkoxysilanes can be aryltrialkoxysilanes, such as, but not limited to, phenyltrimethoxysilane, phenyltriethoxysilane, naphtyltrimethoxysilane, naphtyltriethoxysilane, or any other substituted or unsubstituted aryl trialkoxysilane.

The dialkoxysilanes can be dialkyldialkoxysilanes, diaryldialkoxysilane, or alkylarydialkoxysilanes. Dialkyldialkoxysilanes can be, for example, but not limited to, dimethyldimethoxiysilanes, diethyldimethoxysiloxanes, methylethyldimethoxysilanes, dimethyldiethoxiysilanes, diethyldiethoxysiloxanes, methylethyldiethoxysilanes, or any $(C_xH_{2x+1})_2Si(OC_yH_{2y+1})_2$ silane, where x is independently 1 to 20 and y is 1 to 3. The dialkyldialkoxysilanes can have one or two substituted alkyl groups, where the alkyl group contains one or more ether, hydroxyl, carboxylic acid, carboxylic amide, amino, alkylamino, dialkylamino, cyano group, or any other polar or non-polar group.

The silicate and substituted silicate precursors can be, but is not limited to, a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tridialkyaminoalkylsilane, tri(dialkyamino)arylsilane, di(dialkyamino)dialkylsilane, di(dialkyamino)alkylarylsilane, di(dialkyamino)diarylsilane, or any combination thereof. The alkoxy and dialkylamino groups are generally, but not necessarily, $C_1$ to $C_4$ alkoxy and dialkylamino groups. The alkyl groups are generally, but not necessarily, $C_1$ to $C_4$ groups and aryl groups are generally, but not necessarily phenyl groups. The alkyl and/or phenyl groups can be substituted with a functional group, such as, but not limited to amino, hydroxyl, carboxylic acid, acid anhydride, epoxy, acrylate, methacrylate, and vinyl. The siloxane precursor can be an oligo or polysiloxane that comprises: dialkylsiloxanes; alkylarylsiloxanes; diarylsilanes; alkylhydrogensiloxanes; or any combination thereof. The alky groups include, but are not limited to, methyl, ethyl, n-propyl, isopropyl, n-butyl, sec-butyl, and tert-butyl groups.

The sol can further comprise one or more organic precursors that have functionality that is reactive with the precursor substituents, reactive intermediate substituents, or with the functionality on the siloxy precursors. The organic precursors can be monomeric, oligomeric, or polymeric, where there is at least one functionality on the organic precursor that can react with a reactive precursor substituent, a reactive intermediate substituent, or a reactive functionality of a siloxy precursor in the sol. When the organic precursor has a plurality of functionalities, the organic precursor can react with the functionality of another organic precursor in addition to reacting with a functionality of the sol or the gel that is not of the organic precursor. The organic precursor can have additional functionality for modifying the properties of the gel, functionality that provides an affinity for a target analyte. Polymeric organic precursors can be homopolymers or copolymers, and can have a linear, branched, star-branched, hyper-branched, or dendritic structure. The organic precursors, and functional groups on the siloxy precursors, can be reactive functionality that do not involve hydrolysis and can be functionality that undergo addition or polyaddition reactions rather than condensation reactions to be incorporated into the gel. Organic precursors include, but are not limited to, $\alpha,\omega$-dihydroxyalkanes, $\alpha,\omega$-dihydroxy-poly(ethylene oxide), $\alpha,\omega$-dihydroxy-polypropylene oxide, $\alpha,\omega$-dihydroxy-poly(ethylene oxide-co-propylene oxide), $\alpha,\omega$-dihydroxy-poly(butylene oxide), $\alpha,\omega$-dihydroxy-polyamides, and $\alpha,\omega$-dihydroxy-polyesters. Polymers can be of low degree of polymerization and may be oligomers. The organic precursor can include monomers, oligomers, and/or polymers with pendant reactive functionality, for example, but not limited to, a partially hydroxylated polybutadiene. In addition to hydroxy groups, the reactive groups can be complementary reactive functionality to reactive groups of the siloxane precursors, and can be, but are not limited to, amino, hydroxyl, carboxylic acid, acid anhydride, epoxy, acrylate, methacrylate, and vinyl. Monomeric organic precursors include, but are not limited to, divinylbenzene. Oligomeric organic precursors include, but are not limited to, $\alpha,\omega$-diacrylates of oligoesters. Polymeric organic precursors can be homopolymers, random copolymers, alternating copolymers, block copolymers, or graft-copolymers, and can be linear, branched, hyper-branched, star, or dendritic. The polymers can be homopolymers or copolymers comprising polydimethylsiloxane (PDMS), polytetrahydrofuran (polyTHF), polyethyleneoxide, poly(caprolactone-block-dimethylsiloxane-black-caprolactone) triblock copolymer, 2-hydroxymethyl-18-crown-6, Beta-cyclodextrin, Calix[8]arene, poly(caprolactone-block-tetrahydrofuran-block caprolactone) triblock copolymer, poly(propylene glycol)-block-poly(ethylene glycol)-block-(polypropylene glycol), poly(caprolactone diol), poly(caprolactone triol), chitosan, Dimethylsiloxane-ethylene oxide block copolymer, Carbowax 20M, UCon HTF 14, Chitin, Poly(ethylene glycol)-poly(propylene glycol)-poly(ethylene glycol), and poly(propylene glycol)-poly(ethylene oxide)-poly(propylene glycol). In addition, macromers such as sucrose, sorbitol etc. can also be used.

The sol-gel synthesis can be carried out in a solvent. The solvent can be any solvent that can be removed to a large degree. The solvent can be, but is not limited to, methanol, ethanol, n-propanol, i-propanol, diethyl ether, ethyl acetate, tetrahydrofuran, acetone, methylene chloride, chloroform, acetonitrile, dimethyl sulfoxide, or any compatible mixture thereof. The solvent should be one that can be removed by evaporation or washed from the sol-gel material by a volatile solvent.

In an embodiment of the invention, the sol-gel synthesis is carried out in two steps. A first acid catalyzed hydrolysis step, where a high degree of hydrolysis occurs with a small degree of condensation, is followed by a base catalyzed condensation step. The two-step process allows for a very large surface area, a large fore volume, and a small average pore cross-section. This results in a composite with readily accessible filler within the highly porous matrix.

Figure 2:
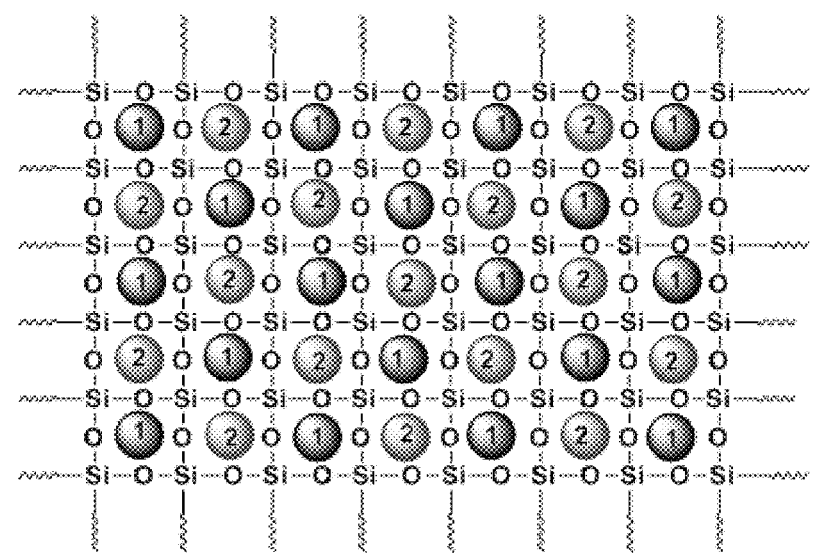
FIG. 2 shows a schematic representation of a carbonaceous and/or non-carbonaceous particulate matters encapsulated in sol-gel sorbent matrix, according to an embodiment of the invention, having a plurality of different particles.
Figure 3:
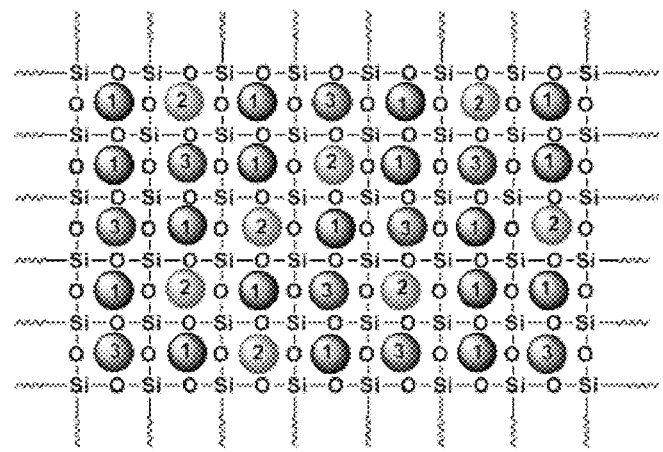
FIG. 3 shows a schematic representation of a carbonaceous and/or non-carbonaceous particulate matters encapsulated in sol-gel sorbent matrix, according to an embodiment of the invention, having a multiplicity of different particles.

The carbonaceous and non-carbonaceous particulate matter encapsulated in sol-gel sorbent matrix is schematically illustrated in FIG. 1 for a single filling particulate matter. It should be understood that the filler need not be: identical in size; periodically dispersed; or that the particle size is sub-nanometer sized to fit into an eight membered siloxane ring. FIG. 2 is a schematically illustration for inclusion of two different particulate matter filler. Again, it should be understood that the fillers need not be: identical in size; periodically dispersed; or that the particle size is sub-nanometer sized to fit into an eight membered siloxane ring. FIG. 3 illustrates the use of a multiplicity of different particulate matter fillers. Again, it should be understood that the filler need not be: identical in size; periodically dispersed; or that the size is sub-nanometer sized to fit into an eight membered siloxane ring.

Figure 4:
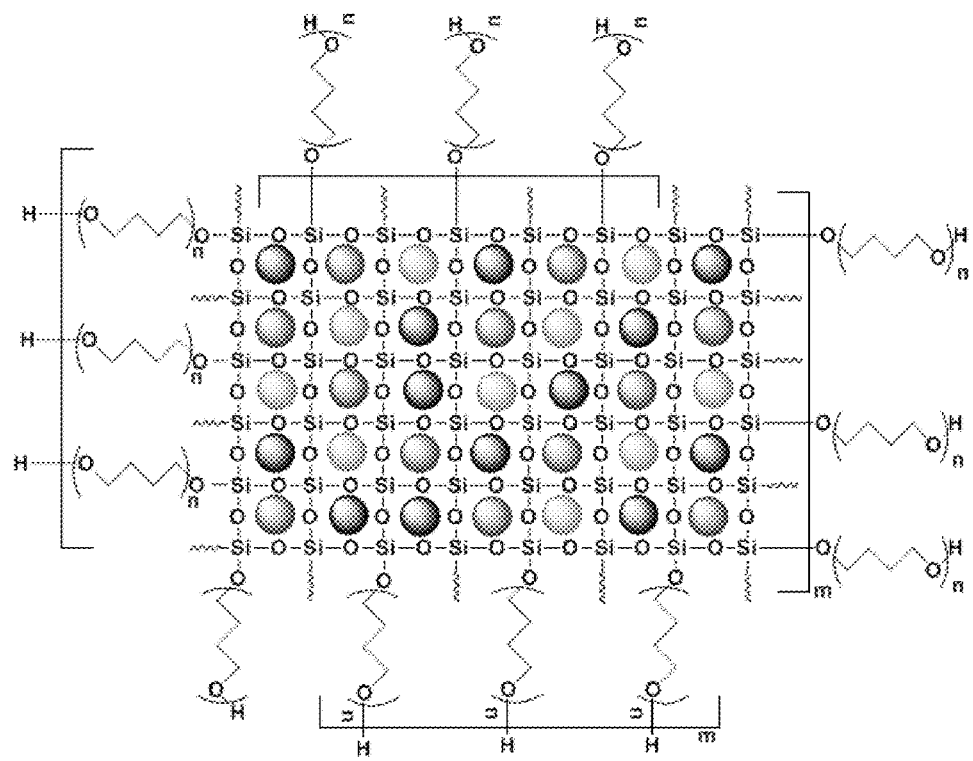
FIG. 4 shows a schematic representation of a carbonaceous and/or non-carbonaceous particulate matters encapsulated in sol-gel sorbent matrix, according to an embodiment of the invention, having polytetrahydrofuran (polyTHF) within the matrix.
Figure 5:
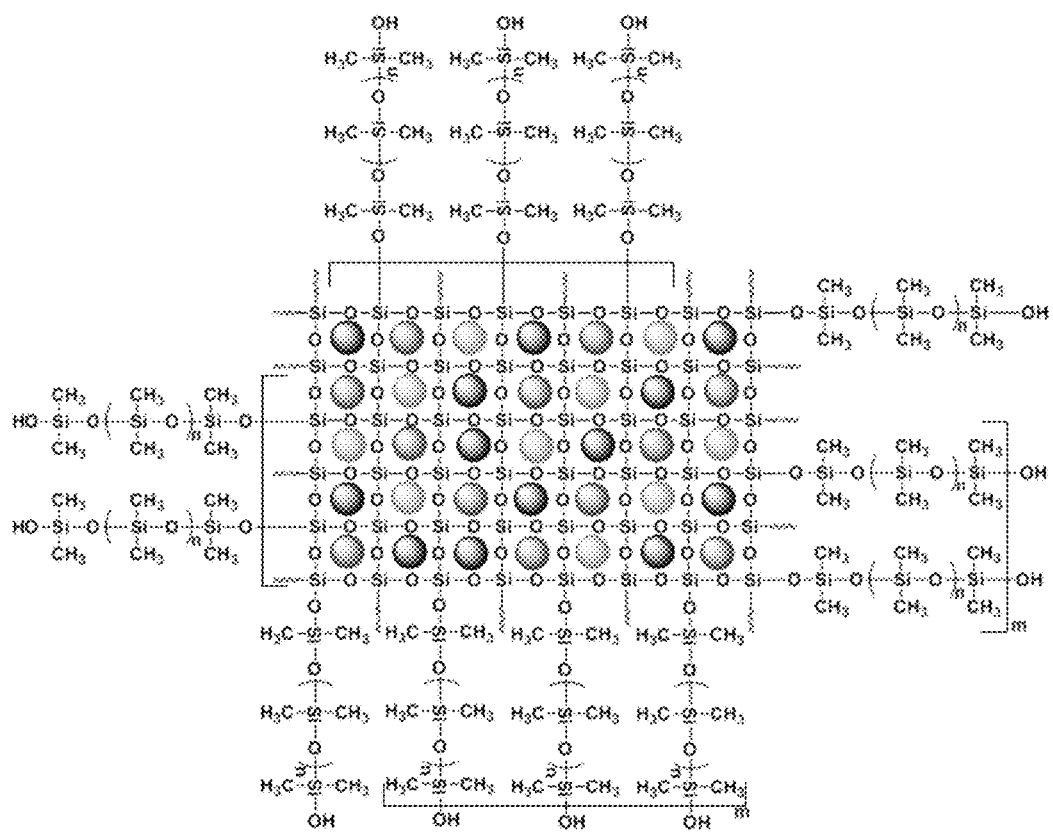
FIG. 5 shows a schematic representation of a carbonaceous and/or non-carbonaceous particulate matters encapsulated in sol-gel sorbent matrix, according to an embodiment of the invention, having polydimethylsiloxane (PDMS) within the matrix.

The carbonaceous and non-carbonaceous particulate matter encapsulated in sol-gel sorbent matrix can include an organic polymer bound within the matrix to partition the filled silica matrix, as illustrated in FIGS. 4 and 5 for a poly(tetrahydrofuran) (PTHF) included and a poly(dimethylsiloxane) (PDMS) included matrix. Again, it should be understood that the fillers need not be: identical in size; periodically dispersed; that the particle size is sub-nanometer sized to fit into an eight membered siloxane ring; or that no filler is situated within a PTHF or PDMS rich phase.

Figure 6A:
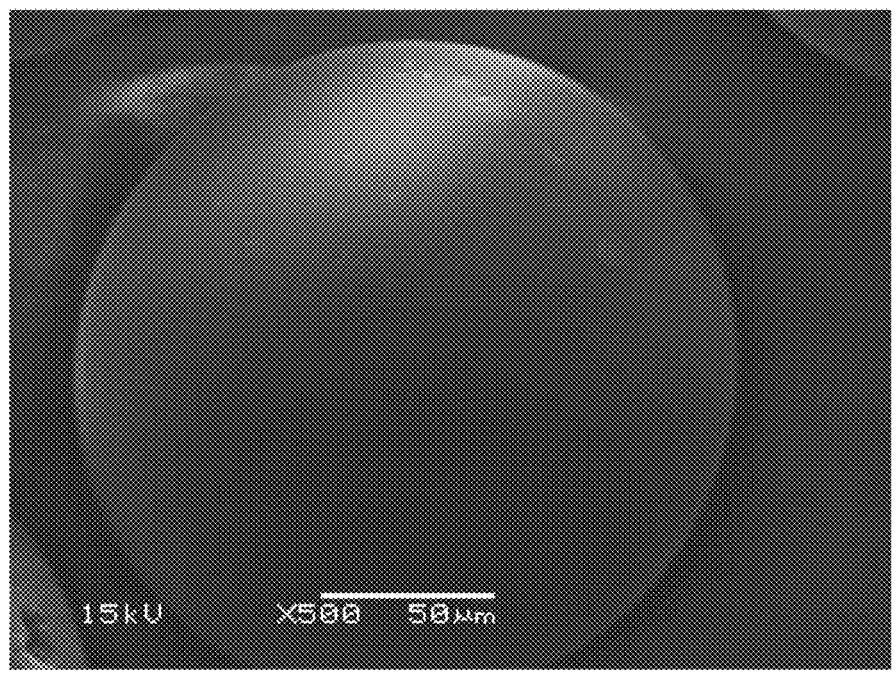
FIG. 6A shows a scanning electron microscopy (SEM) image of pristine CARBOXEN at 500× magnification.
Figure 6B:
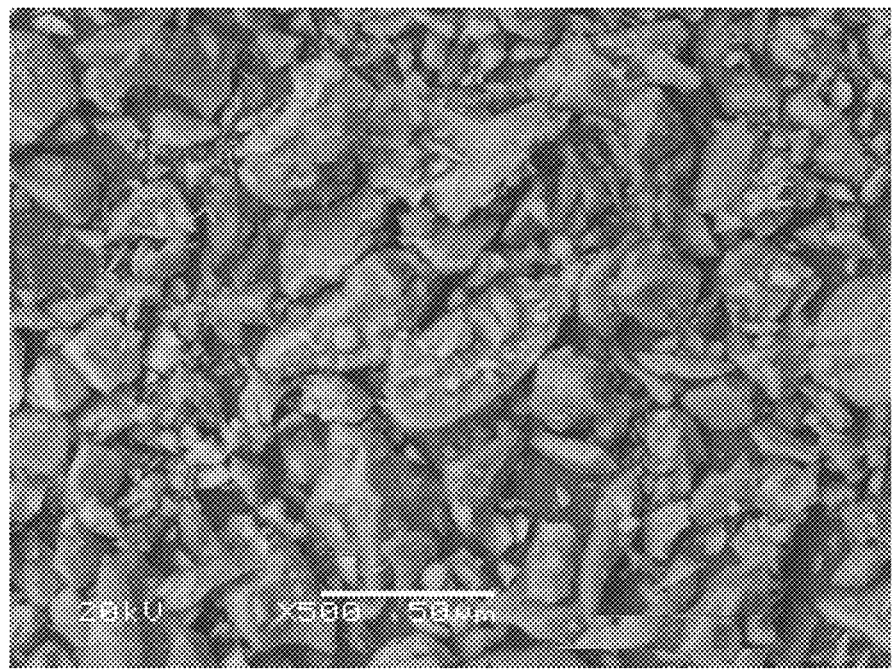
FIG. 6B shows a SEM image of crushed sol-gel PDMS/CARBOXEN, according to an embodiment of the invention, at 500× magnification.
Figure 6C:
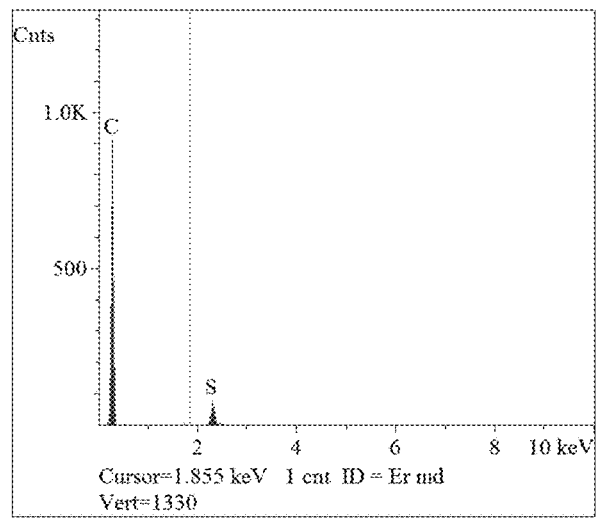
FIG. 6C shows an energy-dispersive X-ray spectroscopy (EDS) spectrum with a table of the non-hydrogen elements contribution to the spectrum for pristine CARBOXEN.
Figure 6D:
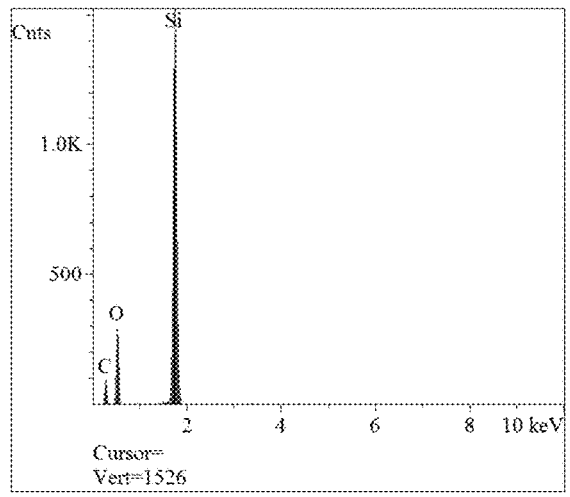
FIG. 6D shows an EDS spectrum with a table of the non-hydrogen elements contribution to the spectrum for crushed sol-gel PDMS/CARBOXEN, according to an embodiment of the invention.
Figure 7A:
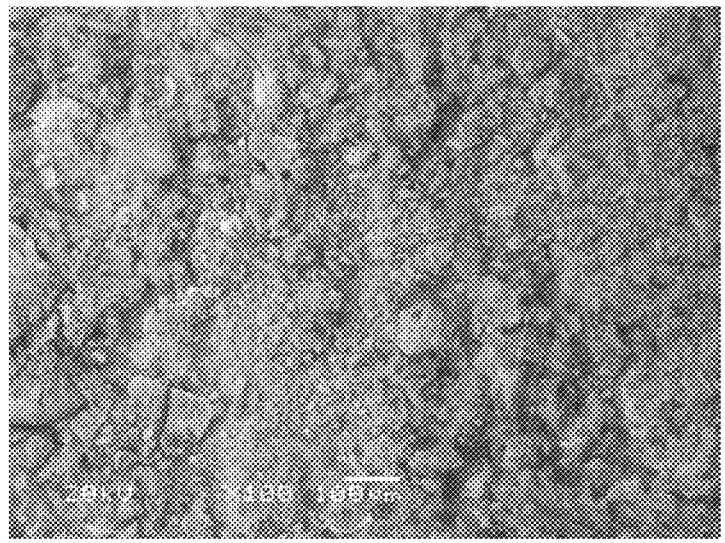
FIG. 7A shows a SEM image of pristine MCM-41 at 100× magnification.
Figure 7B:
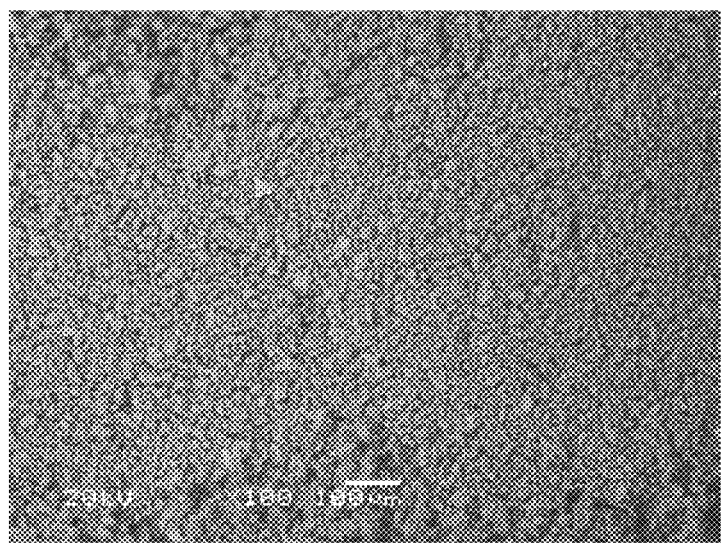
FIG. 7B shows a SEM image of crushed sol-gel PDMS/MCM-41, according to an embodiment of the invention, at 100× magnification.
Figure 7C:
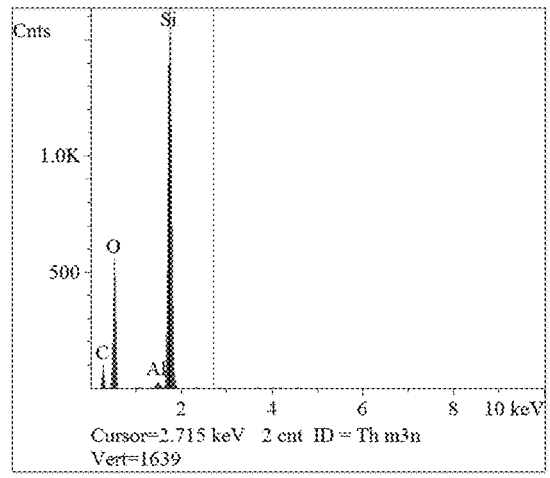
FIG. 7C shows an energy-dispersive X-ray spectroscopy (EDS) spectrum with a table of the non-hydrogen elements contribution to the spectrum for pristine MCM-41.
Figure 7D:
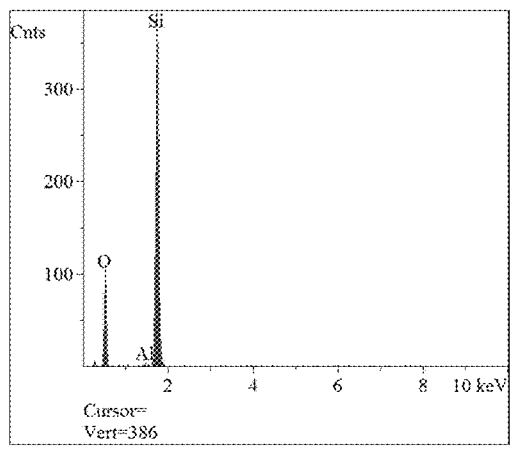
FIG. 7D shows an EDS spectrum with a table of the non-hydrogen elements contribution to the spectrum for crushed sol-gel PDMS/MCM-41, according to an embodiment of the invention.
Figure 8A:
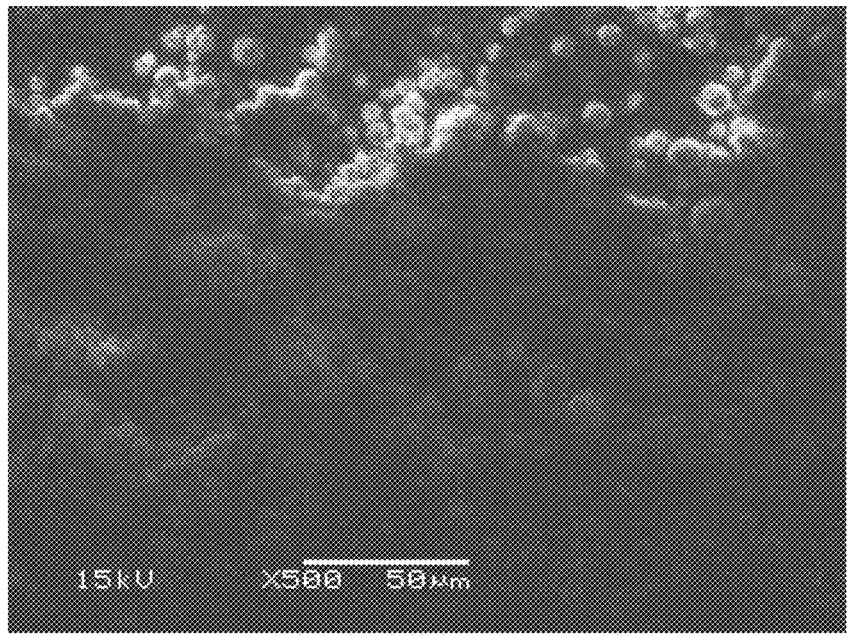
FIG. 8A shows a SEM image of pristine PSDVB at 500× magnification.
Figure 8B:
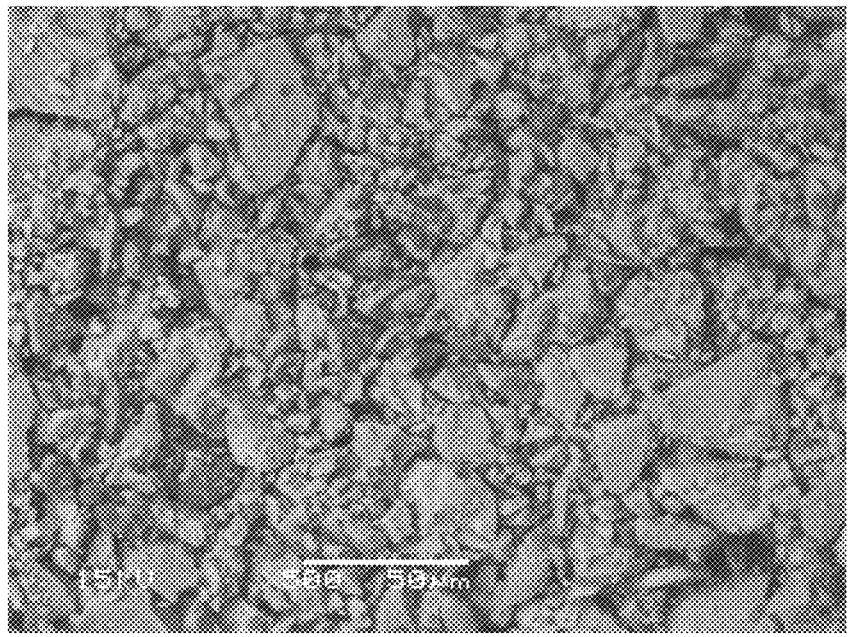
FIG. 8B shows a SEM image of crushed sol-gel PDMS/PSDVB, according to an embodiment of the invention, at 500× magnification.
Figure 8C:
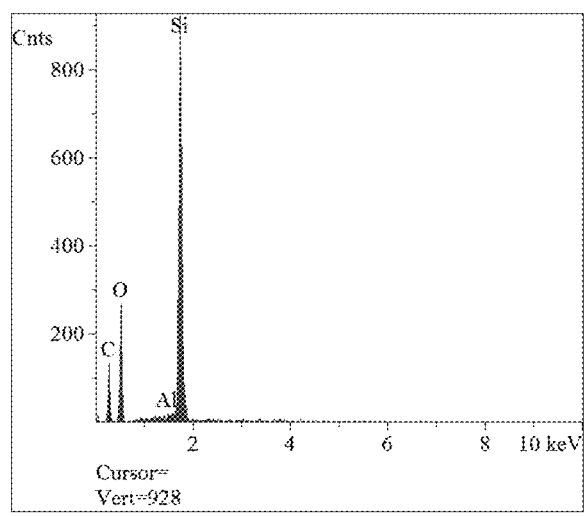
FIG. 8C shows an EDS spectrum with a table of the non-hydrogen elements contribution to the spectrum for crushed sol-gel PDMS/PSDVB, according to an embodiment of the invention.
Figure 9A:
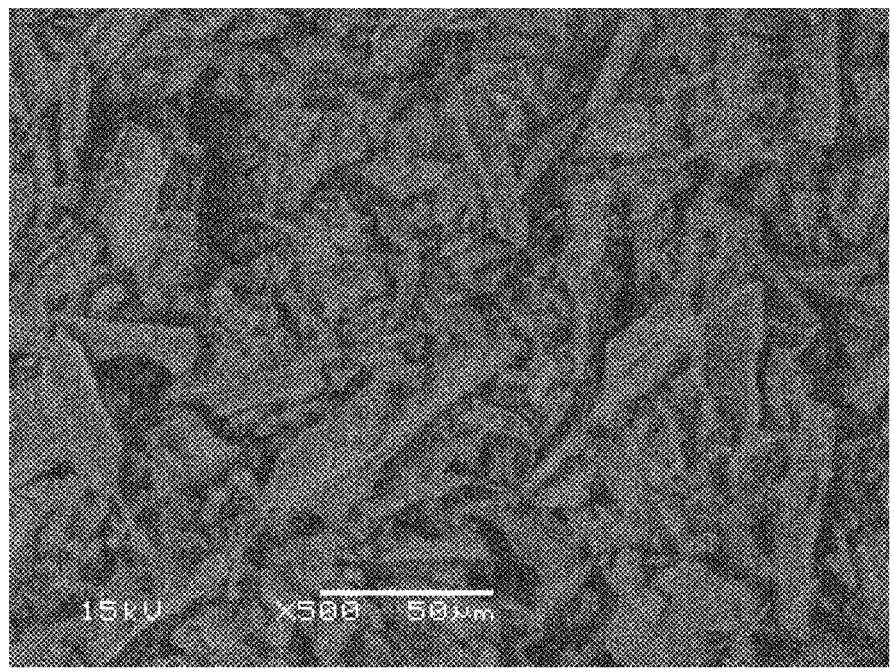
FIG. 9A shows a SEM image of pristine Activated Carbon at 500× magnification.
Figure 9B:
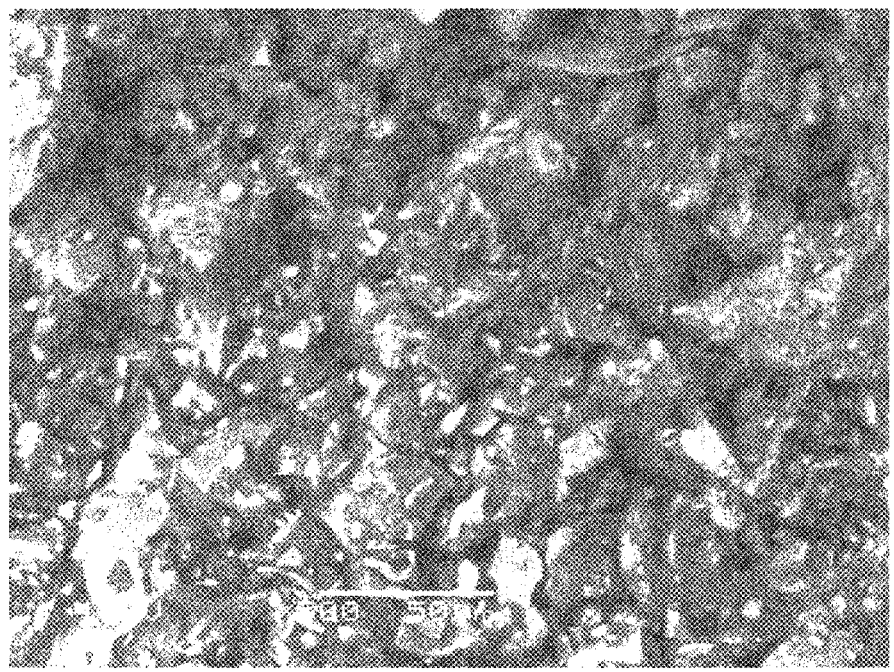
FIG. 9B shows a SEM image of crushed sol-gel PDMS/Activated Carbon, according to an embodiment of the invention, at 500× magnification.
Figure 9C:
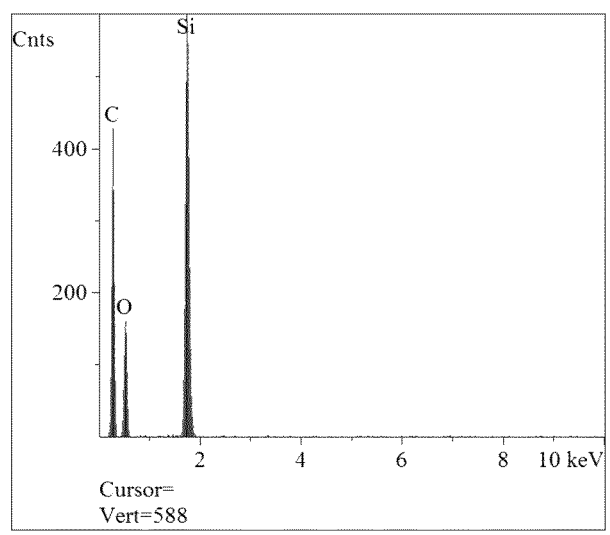
FIG. 9C shows an EDS spectrum with a table of the non-hydrogen elements contribution to the spectrum for crushed sol-gel PDMS Activated Carbon, according to an embodiment of the invention.
Figure 10A:
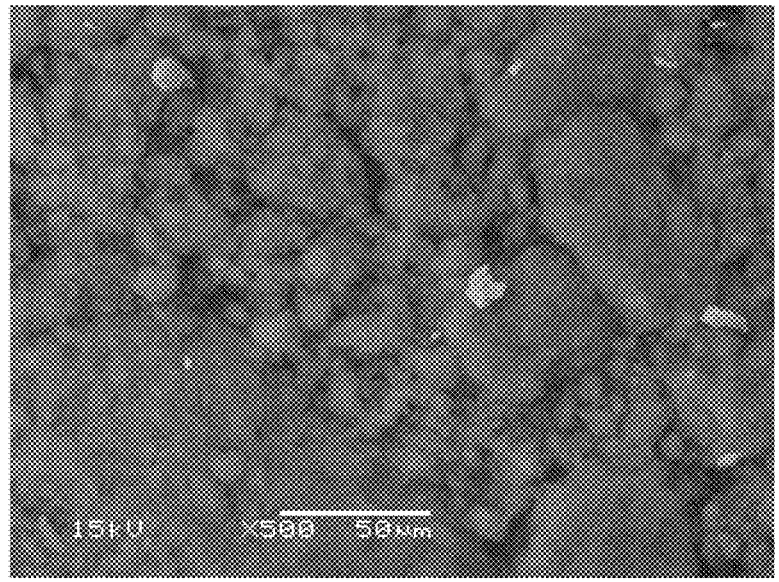
FIG. 10A shows a SEM image of pristine Multi-Wall Carbon Nanotubes at 500× magnification.
Figure 10B:
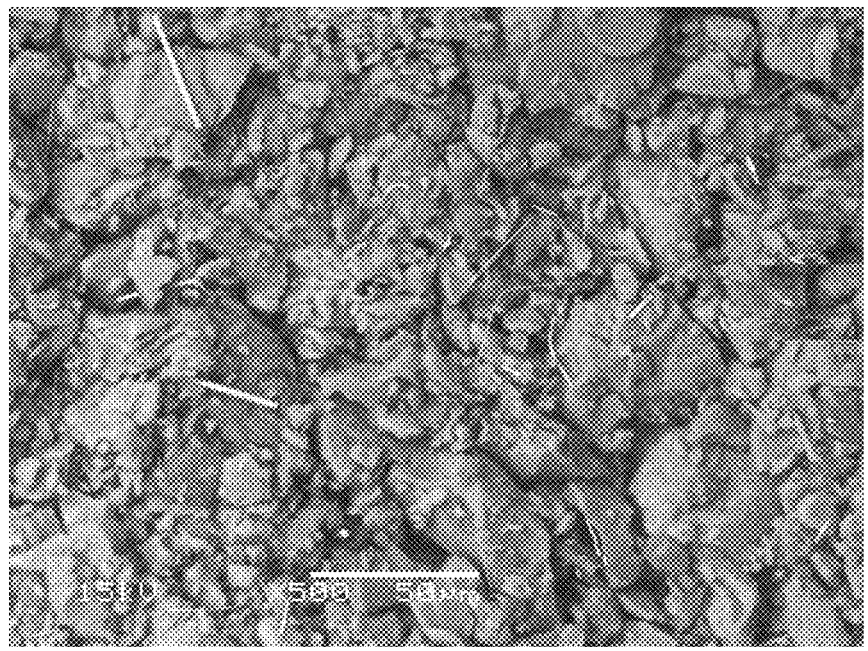
FIG. 10B shows a SEM image of crushed sol-gel PDMS/Multi-Wall Carbon Nanotubes, according to an embodiment of the invention, at 500× magnification.
Figure 10C:
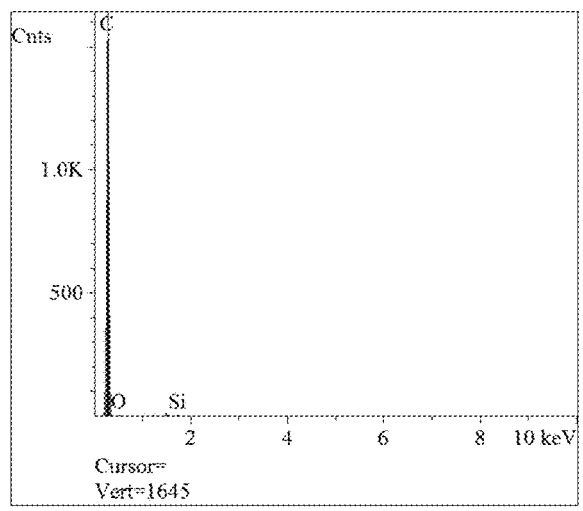
FIG. 10C shows an energy-dispersive X-ray spectroscopy (EDS) spectrum with a table of the non-hydrogen elements contribution to the spectrum for pristine Multi-Wall Carbon Nanotubes.
Figure 10D:
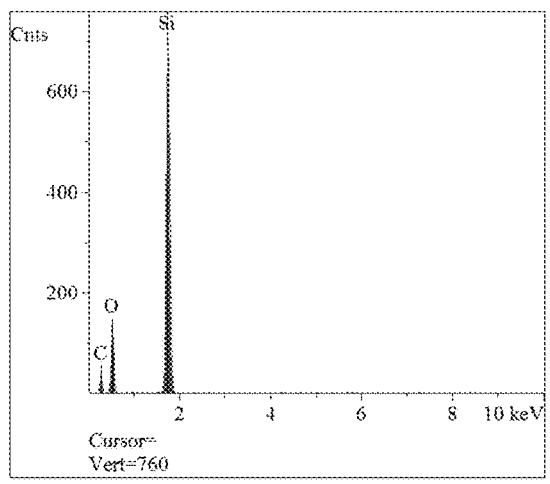
FIG. 10D shows an EDS spectrum with a table of the non-hydrogen elements contribution to the spectrum for crushed sol-gel PDMS/Multi-Wall Carbon Nanotubes, according to an embodiment of the invention.
Figure 11A:
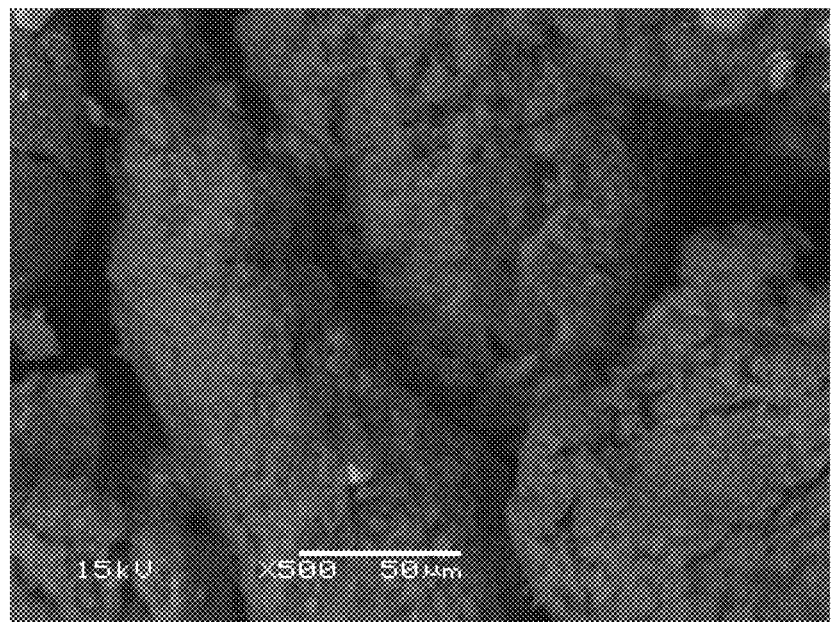
FIG. 11A shows a SEM image of pristine TENAX at 500× magnification.
Figure 11B:
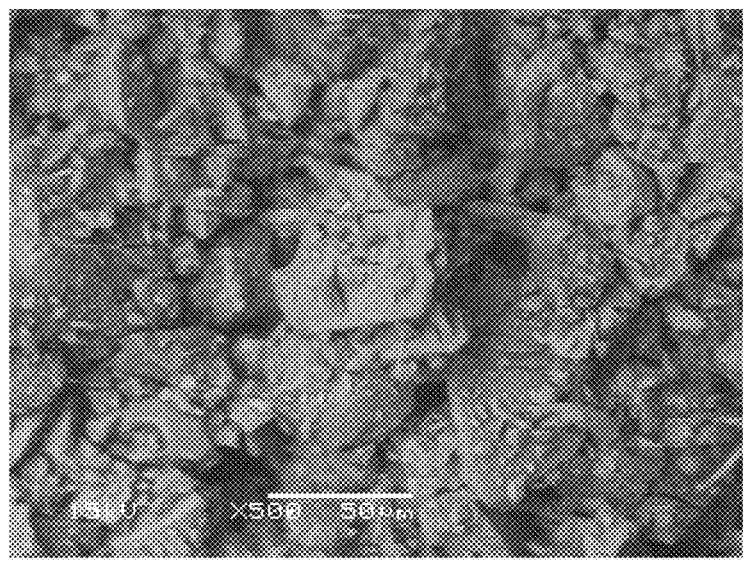
FIG. 11B shows a SEM image of crushed sol-gel PDMS/TENAX, according to an embodiment of the invention, at 500× magnification.
Figure 11C:
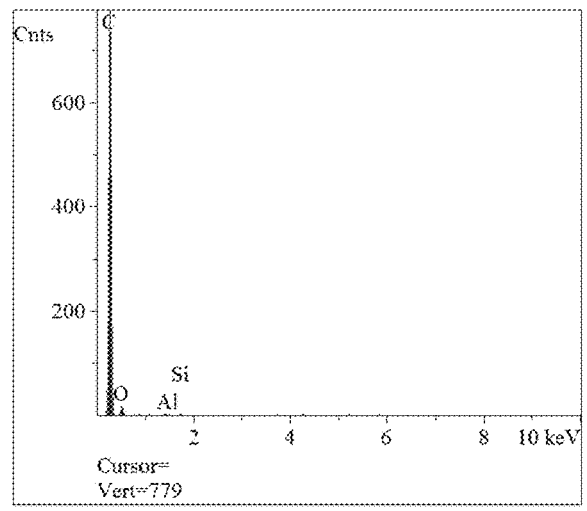
FIG. 11C shows an energy-dispersive X-ray spectroscopy (EDS) spectrum with a table of the non-hydrogen elements contribution to the spectrum for pristine TENAX.
Figure 11D:
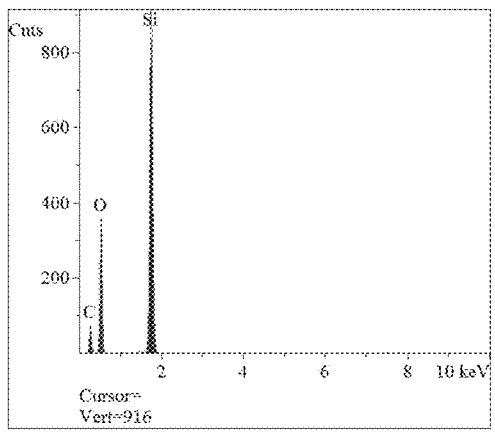
FIG. 11D shows an EDS spectrum with a table of the non-hydrogen elements contribution to the spectrum for crushed sol-gel PDMS/TENAX, according to an embodiment of the invention.
Figure 12A:
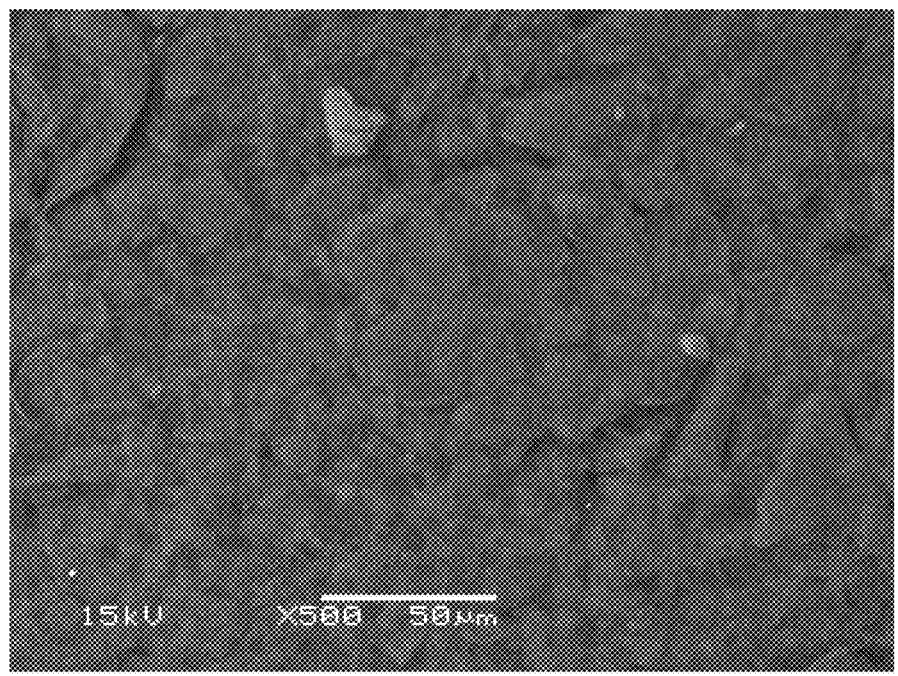
FIG. 12A shows a SEM image of pristine Graphene at 500× magnification.
Figure 12B:
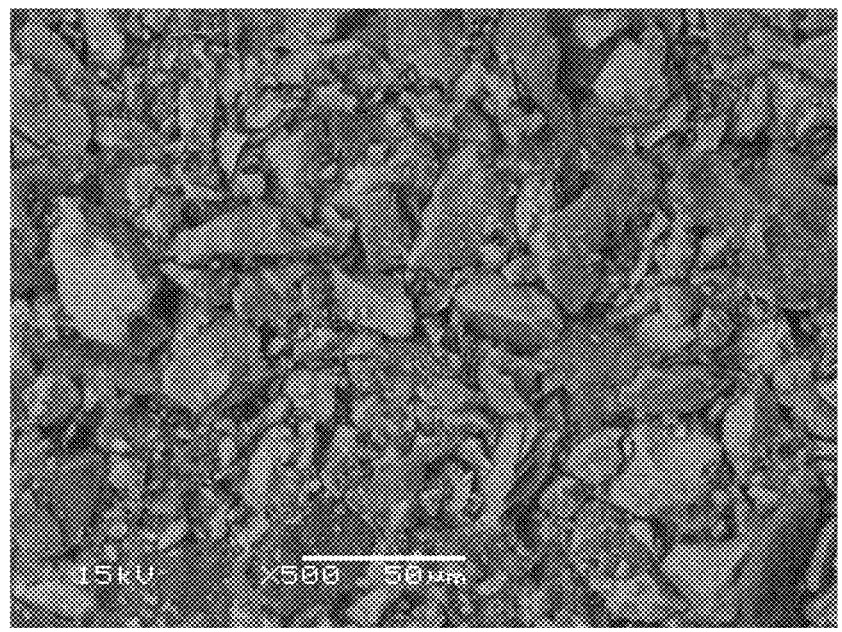
FIG. 12B shows a SEM image of crushed sol-gel PDMS/Graphene, according to an embodiment of the invention, at 500× magnification.
Figure 12C:
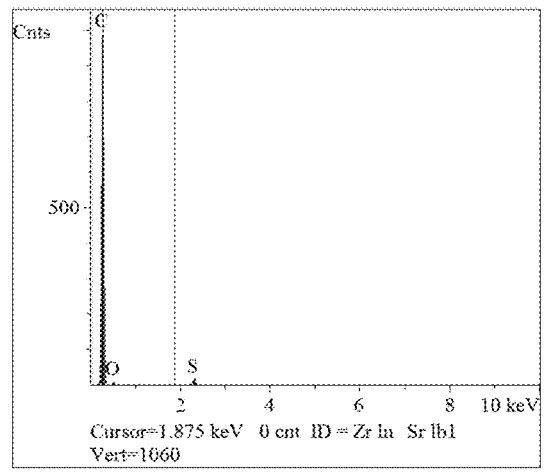
FIG. 12C shows an energy-dispersive X-ray spectroscopy (EDS) spectrum with a table of the non-hydrogen elements contribution to the spectrum for pristine Graphene.
Figure 12D:
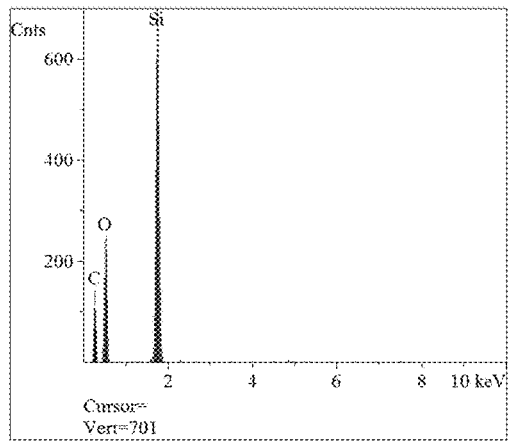
FIG. 12D shows an EDS spectrum with a table of the non-hydrogen elements contribution to the spectrum for crushed sol-gel PDMS/Graphene, according to an embodiment of the invention.

The sol-gel reaction is carried out in the presence of the dispersed particulate filler or fillers. The dispersed particles are combined with the sol-gel precursors and the two-step sol-gel reaction sequence is carried out. Any residual solvent is removed by evaporation or by washing with water or a more volatile solvent. The resulting monolith is typically crushed into sub-millimeter particles. Upon crushing, the particles can be fractured in addition to the matrix. The exposed surface of the crushed carbonaceous particulate matter encapsulated in sol-gel sorbent matrix can include the surface of the particle, for example, a surface that had been internal to a particle, as is suggested by comparison of FIGS. 6A and 6B, which displays an SEM image of a carboxen particle and of carboxen particles encapsulated silica-PDMS sol-gel matrix, according to an embodiment of the invention respectively. Although the images indicate the crushing of carboxen particles, the Energy-dispersive X-ray Spectra (EDS) of the crushed particles clearly have a majority sol-gel PDMS matrix relative to that of pristine carboxen, as can be seen in FIGS. 6C and 6D. In like manner, the non-carbonaceous particulate matter encapsulated in sol-gel sorbent matrix is illustrated in FIGS. 7A-7D for a Mobil Composition of Matter No. 41 (MCM-41) particles encapsulated silica-PDMS sol-gel matrix. In like manner, the carbonaceous particulate matter encapsulated in sol-gel sorbent matrix is illustrated in FIGS. 8A-8C for a polystyrene-divinylbenzene (PSDVB) particles encapsulated silica- PDMS sol-gel matrix. In like manner, the carbonaceous particulate matter encapsulated in sol-gel sorbent matrix is illustrated in FIGS. 9A-9C for an Activated Carbon particles encapsulated silica-PDMS sol-gel matrix. In like manner, the carbonaceous particulate matter encapsulated in sol-gel sorbent matrix is illustrated in FIGS. 10A-10D for Multi-Wall Carbon Nanotubes encapsulated silica-PDMS sol-gel matrix. In like manner, the non-carbonaceous particulate matter encapsulated in sol-gel sorbent matrix is illustrated in FIGS. 11A-11D for TENAX particles encapsulated silica-PDMS sol-gel matrix. In like manner, the carbonaceous particulate matter encapsulated in sol-gel sorbent matrix is illustrated in FIGS. 12A-12D for Graphene particles encapsulated silica-PDMS sol-gel matrix.

Figure 13:
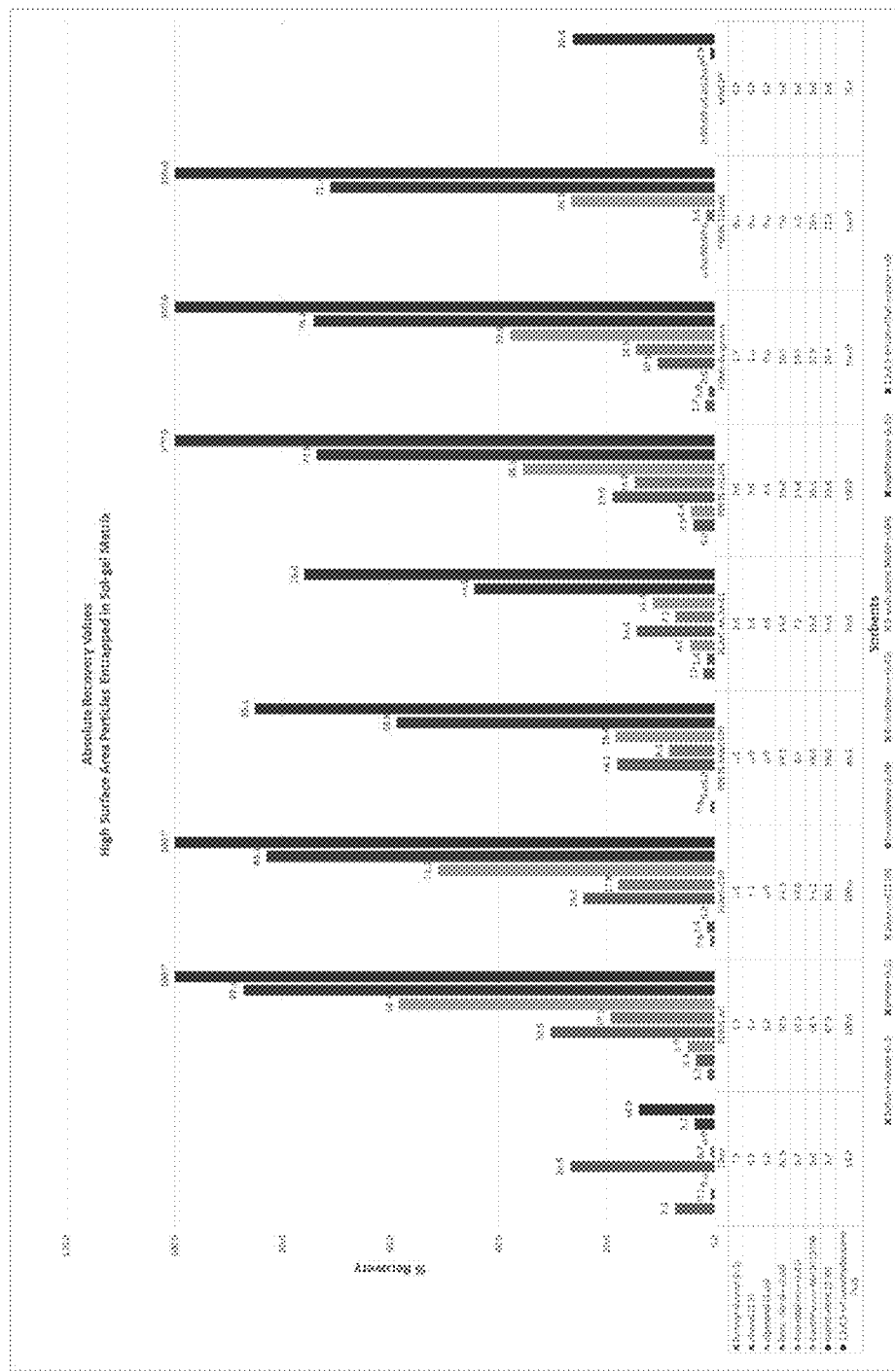
FIG. 13 shows a bar chart of absorption by carbonaceous and non-carbonaceous particulate matters encapsulated in sol-gel sorbent matrices, according to an embodiment of the invention, where the % recovery from a solution containing nine analytes showed differing affinities for the nine analytes depending on the particulate matter encapsulated.

The bar chart of FIG. 13 shows how the carbonaceous and non-carbonaceous particulate matter encapsulated in sol-gel sorbent matrices indicated above perform as sorbents for nine different analytes in comparison to sol-gel silica sorbent. The sol-gel silica sorbent had the highest absorbance for only one of the nine analytes. The sol-gel portion is common to all sol-gel composite sorbents, according to an embodiment of the invention, but differs in organic polymer and particulate material(s). The impact of the inclusion of organic polymer and particulate materials are substantial as evident in the absolute extraction recovery presented in the table and graph presented in FIG. 13. It should be understood that the examples and embodiments described herein are for illustrative purposes only and that various modifications or changes in light thereof will be suggested to persons skilled in the art and are to be included within the spirit and purview of this application.

We claim:

1. A particulate sorbent, comprising a carbonaceous and/or non-carbonaceous nanoparticle or microparticles encapsulated in sol-gel sorbent matrix, the sol-gel matrix comprising a porous sol-gel metal oxide network from hydrolysis and condensation of metal oxide precursors:

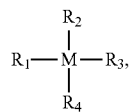

wherein M is silicon, titanium, aluminum, zirconium, germanium, barium, gallium, indium, thallium, vanadium, cobalt, nickel, chromium, copper, iron, zinc, or boron; and $R_1$, $R_2$, $R_3$ and $R_4$ are substituents groups, at least two of which are alkoxy, hydroxy, halide, or dialkylamino, and the remaining $R_1$, $R_2$, $R_3$ and $R_4$ are independently absent or comprise alkyl moieties, arylene moieties, cyanoalkyl moieties, fluoroalkyl moieties, phenyl moieties, cyanophenol moieties, biphenyl moieties, cyanobiphenyl moieties, dicyanobiphenyl, cyclodextrin moieties, crown ether moieties, cryptand moieties, calixarene moieties, or any derivative thereof.

2. The particulate sorbent according to claim 1, wherein 1 to 100% of the metals of the metal oxide have substituents that are one or more $C_1$ to $C_4$ alkyl group and/or one or more aryl groups.

3. The particulate sorbent according to claim 2, wherein one or more of the $C_1$ to $C_4$ alkyl group and/or one or more of the aryl groups is substituted with a functional group.

4. The particulate sorbent according to claim 1, wherein the sol-gel metal oxide network comprises a plurality of polymer segments from polymeric organic precursors.

5. The particulate sorbent according to claim 4, wherein the polymer segments bridge between two or more metals of the sol-gel metal oxide network.

6. The particulate sorbent according to claim 5, wherein the polymer segments bridges between 1 and 50 percent of the metals of the sol-gel metal oxide network.

7. The particulate sorbent according to claim 5, wherein the polymer segments comprise polydimethylsiloxane (PDMS), polytetrahydrofuran (polyTHF), polyethyleneoxide, poly(caprolactone-block-dimethylsiloxane-black-caprolactone) triblock copolymer, 2-hydroxymethyl-18-crown-6, Beta-cyclodextrin, Calix[8]arene, poly(caprolactone-block-tetrahydrofuran-block caprolactone) triblock copolymer, poly(propylene glycol)-block-poly(ethylene glycol)-block-(polypropylene glycol), poly(caprolactone diol), poly(caprolactone triol), chitosan, Dimethylsiloxane-ethylene oxide block copolymer, Carbowax 20M, UCon HTF 14, Chitin, Poly(ethylene glycol)-poly(propylene glycol)-poly(ethylene glycol), poly(propylene glycol)-poly(ethylene oxide)-poly(propylene glycol), sucrose, or sorbitol.

8. The particulate sorbent according to claim 1, wherein the carbonaceous nanoparticle or microparticles comprises carboxen, activated carbon, graphene, carbon nanotubes, polystyrenedivinylbenzene resin, polyacrylate-polyalcohol, polypyrrole, Amberlite XAD-2, Amberjet 4200, Dowex MB Mixed Ion Exchange Resin, or Amberlyst 15.

9. The particulate sorbent according to claim 1, wherein the non-carbonaceous nanoparticles or microparticles comprise MCM-41, Tenax, silica, alumina, zirconia, or kaoline.

10. A method of preparing a particulate sorbent according to claim 1, comprising:
   providing a plurality of carbonaceous and/or non-carbonaceous nanoparticle or microparticles;
   providing a plurality of metal oxide precursors;
   optionally, providing a plurality of polymers comprising at least one functional group capable of undergoing reaction with the metal oxide precursor;
   combining the plurality of carbonaceous and/or non-carbonaceous particulate mater with the plurality of metal oxide precursors, optionally, the plurality of polymers, and, optionally, a solvent to make a sol mixture;
   adding water and an acid catalyst to the sol mixture;
   hydrolyzing the plurality of metal oxide precursors to a hydrolyzed sol mixture;
   adding a base to the hydrolyzed sol mixture;
   condensing the hydrolyzed sol mixture to a gel; and
   fracturing the gel into sorbent particles of a carbonaceous and/of non-carbonaceous particulate matter encapsulated in sol-gel sorbent matrix.

11. The method according to claim 10, wherein the carbonaceous and/or non-carbonaceous particulate maters comprise carboxen, activated carbon, graphene, carbon nanotubes, polystyrenedivinylbenzene resin, MCM-41, Tenax, silica, alumina, or zirconia.

12. The method according to claim 10, wherein the metal oxide precursors comprises:

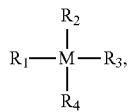

wherein M is silicon, titanium, aluminum, zirconium, germanium, barium, gallium, indium, thallium, vanadium, cobalt, nickel, chromium, copper, iron, zinc, or boron, $R_1$, $R_2$, $R_3$ and $R_4$ are substituents groups, at least two of which are alkoxy, hydroxy, halide, or dialkylamino, and the remaining $R_1$, $R_2$, $R_3$ and $R_4$ are independently absent or comprise alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof.

13. The method according to claim 10, wherein the polymer comprises polydimethylsiloxane (PDMS), polytetrahydrofuran (polyTHF), polyethyleneoxide, poly(caprolactone-block-dimethylsiloxane-black-caprolactone) triblock copolymer, 2-hydroxymethyl-18-crown-6, Beta-cyclodextrin, Calix[8]arene, poly(caprolactone-block-tetrahydrofuran-block caprolactone) triblock copolymer, poly(propylene glycol)-block-poly(ethylene glycol)-block-(polypropylene glycol), poly(caprolactone diol), poly(caprolactone triol), chitosan, dimethylsiloxane-ethylene oxide block copolymer, Carbowax 20M, UCon HTF 14, Chitin, Poly(ethylene glycol)-poly(propylene glycol)-poly(ethylene glycol), poly(propylene glycol)-poly(ethylene oxide)-poly(propylene glycol), sucrose, or sorbitol.

14. The method according to claim 10, wherein fracturing comprises grinding or milling.

15. A method of collecting or separating, comprising:
providing a particulate sorbent according to claim 1; and
contacting the particulate sorbent with a fluid comprising analytes.

16. The method according to claim 15, wherein contacting comprises introducing the particulate sorbent to the fluid.

17. The method according to claim 16, wherein introducing comprises solid phase extraction or solid phase microextraction.

18. The method according to claim 15, wherein contacting comprises introducing the fluid to the particulate sorbent.

19. The method according to claim 18, wherein introducing comprises water filtrating, air entrainment, and chromatographic separation.

* * * * *